US008318666B2

(12) United States Patent
DePaoli et al.

(10) Patent No.: US 8,318,666 B2
(45) Date of Patent: *Nov. 27, 2012

(54) USE OF LEPTIN TO TREAT METABOLIC ABNORMALITIES ASSOCIATED WITH LIPOATROPHY

(75) Inventors: Alexander M. DePaoli, Santa Barbara, CA (US); Elif Arioglu Oral, Ann Arbor, MI (US); Simeon I. Taylor, Skillman, NJ (US); Abhimanyu Garg, Dallas, TX (US)

(73) Assignees: Amgen, Inc., Thousand Oaks, CA (US); The United States of America, as Represented by the Secretary, Department of Health and Human Services, Washington, DC (US); Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/103,294

(22) Filed: May 9, 2011

(65) Prior Publication Data

US 2011/0306540 A1  Dec. 15, 2011

Related U.S. Application Data

(60) Division of application No. 11/606,805, filed on Nov. 29, 2006, which is a division of application No. 10/623,189, filed on Jul. 18, 2003, now Pat. No. 7,183,254, which is a continuation of application No. 10/279,129, filed on Oct. 22, 2002, now abandoned.

(60) Provisional application No. 60/336,394, filed on Oct. 22, 2001.

(51) Int. Cl.
*A61K 38/00* (2006.01)
*A61K 38/22* (2006.01)
*A61P 3/06* (2006.01)

(52) U.S. Cl. ............................. 514/5.8; 514/7.4
(58) Field of Classification Search ........................ None
See application file for complete search history.

(56) References Cited

U.S. PATENT DOCUMENTS

| | | | |
|---|---|---|---|
| 5,521,283 A | 5/1996 | DiMarchi et al. |
| 5,525,705 A | 6/1996 | DiMarchi et al. |
| 5,532,336 A | 7/1996 | DiMarchi et al. |
| 5,552,522 A | 9/1996 | DiMarchi et al. |
| 5,552,523 A | 9/1996 | Basinski et al. |
| 5,552,524 A | 9/1996 | Basinski et al. |
| 5,554,727 A | 9/1996 | Basinski et al. |
| 5,559,208 A | 9/1996 | Basinski et al. |
| 5,563,243 A | 10/1996 | DiMarchi et al. |
| 5,563,244 A | 10/1996 | DiMarchi et al. |
| 5,563,245 A | 10/1996 | DiMarchi et al. |
| 5,567,678 A | 10/1996 | DiMarchi et al. |
| 5,567,803 A | 10/1996 | Basinski et al. |
| 5,569,743 A | 10/1996 | DiMarchi et al. |
| 5,569,744 A | 10/1996 | Basinski et al. |
| 5,574,133 A | 11/1996 | DiMarchi et al. |
| 5,580,954 A | 12/1996 | DiMarchi et al. |
| 5,594,101 A | 1/1997 | Becker et al. |
| 5,594,104 A | 1/1997 | Basinski et al. |
| 5,605,886 A | 2/1997 | Basinski et al. |
| 5,614,379 A | 3/1997 | MacKellar |
| 5,691,309 A | 11/1997 | Basinski et al. |
| 5,719,266 A | 2/1998 | DiMarchi et al. |
| 5,756,461 A | 5/1998 | Stephens |
| 5,922,678 A | 7/1999 | Stephens |
| 6,258,932 B1 | 7/2001 | Vahlne |
| 6,899,892 B2 | 5/2005 | Gallahar et al. |

FOREIGN PATENT DOCUMENTS

| | | |
|---|---|---|
| EP | 0 725 078 | 8/1996 |
| EP | 0 725 079 | 8/1996 |
| EP | 0 736 599 | 10/1996 |
| EP | 0 741 187 | 11/1996 |
| EP | 0 744 408 | 11/1996 |
| EP | 0 745 610 | 12/1996 |
| EP | 0 835 879 | 4/1998 |
| WO | WO 96/05309 | 2/1996 |
| WO | WO 96/22308 | 7/1996 |
| WO | WO 96/23513 | 8/1996 |
| WO | WO 96/23514 | 8/1996 |
| WO | WO 96/23515 | 8/1996 |
| WO | WO 96/23516 | 8/1996 |
| WO | WO 96/23517 | 8/1996 |
| WO | WO 96/23518 | 8/1996 |
| WO | WO 96/23519 | 8/1996 |
| WO | WO 96/27385 | 9/1996 |
| WO | WO 96/31526 | 10/1996 |

(Continued)

OTHER PUBLICATIONS

Abate, N., et al., "Estimation of Adipose Tissue Mass by Magnetic Resonance Imaging: Validation Against Dissection in Human Cadavers," J. Lipid Res., 1994, 1490-1496, vol. 35.
Ahima, R.S., et al., "Role of Leptin in the Neuroendocrine Response to Fasting," Nature, 1996, 250-252, vol. 382.
Arioglu, E., et al., "Efficacy and Safety of Troglitazone in the Treatment of Lipodystrophy Syndromes," An Intern Med., 2000, 263-274, vol. 133.
Arslanian, eta I., Metabolism. 47: 309-312, 1998.
Berasain, C, et al., "Pathological and Virological Findings in Patients With Persistent Hypertransaminassaemia of Unknown Etiology," Gut, 2000, 429-435, vol. 47.

(Continued)

*Primary Examiner* — Gyan Chandra
(74) *Attorney, Agent, or Firm* — Amylin Pharmaceuticals, LLC

(57) ABSTRACT

Leptin, leptin analogs, and leptin derivatives are used to treat patients with lipoatrophy. Leptin is effective against conditions of lipoatrophy for both genetic and acquired forms of the disease. A therapeutically effective amount of leptin can be administered in a variety of ways, including subcutaneously and using gene therapy methods. Methods of the present invention contemplate administration of leptin, leptin analogs, and leptin derivatives to patients having a leptin level of approximately 4 ng/ml or less before treatment.

35 Claims, 6 Drawing Sheets

FOREIGN PATENT DOCUMENTS

| | | |
|---|---|---|
| WO | WO 96/34111 | 10/1996 |
| WO | WO 96/34885 | 11/1996 |
| WO | WO 96/35787 | 11/1996 |
| WO | WO 96/37517 | 11/1996 |
| WO | WO 96/40912 | 12/1996 |
| WO | WO 97/00886 | 1/1997 |
| WO | WO 97/06816 | 2/1997 |
| WO | WO 97/16550 | 5/1997 |
| WO | WO 97/18833 | 5/1997 |
| WO | WO 97/20933 | 6/1997 |
| WO | WO 97/38014 | 10/1997 |
| WO | WO 97/46585 | 12/1997 |
| WO | WO 98/08512 | 3/1998 |
| WO | WO 98/28427 | 7/1998 |
| WO | WO 00/20872 | 4/2000 |

OTHER PUBLICATIONS

Berg, A.H., et al., "The Adipocyte-Secreted Protein Acrp30 Enhances Hepatic Insulin Action," Nat. Med., 2001, 947-953, vol. 7.

Berg, J.P., "Leptin is a Potent Anti-Diabetic in Mice with Lipodystrophy and Insulin Resistance," European Journal of Endocrinology, 2000, 114-116, vol. 142.

Burant, C.F., et al., "Troglitazone Action is Independent of Adipose Tissue," J. Clin. Invest, 1997, 2900-2908; vol. 100.

Campfield, L.A., et al., "Recombinant Mouse OB Protein: Evidence for a Peripheral Signal Linking Adiposity and Central Neural Networks," Science, 1995, 546-549, vol. 269.

Cao, H., et al., "Nuclear Lamin A/C R482q Mutation in Canadian Kindreds With Cunningan-Type Familial Partial Lipodystrophy," Hum. Mol. Genet., 2000, 109-112, vol. 9.

Cosidine, R.V., et al., "Serum Immunoreactive-Leptin Concentrations in Normal-Weight and Obese Humans," N. Engl. J. Med., 1996, 292-295, vol. 334.

Ebihara, K., et al., "Transgenic Overexpression of Leptin Rescues Insulin Resistance and Diabetes in a Mouse Model of Lipoatrophic Diabetes," Diabetes, 2001 1440-1448, vol. 50.

European Patent Office, Supplementary European Search Report for EP 02793811, Mar. 20, 2006.

Farooqi, I.S., et al., "Effects of Recombinant Leptin Therapy in a Child With Congenital Leptin Deficiency," N. Engl. J. Med., 1999, 879-884, vol. 341.

Feskanich, D., et al., "Reproducibility and Validity of Food Intake Measurements From a Semiquantitative Food Frequency Questionnaire," J. Am. Diet Assoc, 1993, 790-796, vol. 93.

Fruebis, J., et al., "Proteolytic Cleavage Prodcut of 30-Kda Adipocyte Complement-Related Protein Increases Fatty Acid Oxidation in Muscle and Causes Weight Loss in Mice," Proc. Natl. Acad. Sci. USA, 2001, 2005-2010, vol. 98.

Garg, A., et al., "Adipose Tissue Distribution Pattern in Patients with Familiar Partial Lipodystrophy (Dunnigan Variety)," J. Clin. Endocrinol. Metab., 1999, 170-174, vol. 84.

Garg, A., et al., "Peculiar Distribution of Adipose Tissue in Patients With Congenital Generalized Lipodystrophy," J. Clin. Endocrinol. Metab., 1992, 358-361, vol. 75.

Garg, A., et al., "Lipodystrophies," Am. J. Med., 2000, 143-152, vol. 108.

Gavrilova, O., et al., "Surgical Implantation of Adipose Tissue Reverses Diabetes in Lipoatrophic Mice," J. Clin. Invest., 2000, 271-278, vol. 105.

Gotto, A.M., Jr., "Triglyceride as a Risk Factor for Coronary Artery Disease," Am. J. Cariol., 1998, 22Q-25Q, vol. 82.

Halaas, J.L., et al., "Weight-Reducing Effects of the Plasma Protein Encoded by the Obese Gene," Science, 1995, 543-546, vol. 269.

Hanaki, et al., J. Clin. Endocr. Metab. 84: 1524-1526, 1999.

Harrision, L.C., et al., "Correlation Between Insulin Receptor Binding in Isolated Fat Cells and Insulin Sensitivity in Obese Human Subjects," J. Clin. Invest., 1976, 1435-1441, vol. 58.

Heymsfield, S.B., et al., "Recombinant Leptin for Weight Loss in Obese and Lean Adults: A Randomized, Controlled, Dose-Escalation Trial [See Comments]," JAMA, 1999, 1568-1575, vol. 282.

"Intensive Blood-Glucose Control With Sulphonylureas or Insulin Compared With Conventional Treatment and Risk of Complications in Patients with Type 2 Diabetes (UKPDS33)," UK Prospective Diabetes Study (UKPDS) Group, Lancet, 1998, 837-853; vol. 352.

Jaquet, D., et al., "Extremely Low Values of Serum Leptin in Children With Congenital Generalized Lipoatrophy," European Journal of Endocrinology, 1999. 107-109, vol. 140, No. 1.

Kreisberg, R.A., "Diabetic Dyslipidemia," Am. J. Cardiol., 1998, 67U-73U, vol. 82.

Lambrinoudaki, I., et al., "Body Composition Assessment by Dual-Energy X-Ray Absorptionmetry: Comparison of Prone and Supine Measurements," Metabolism, 1998, 1379-1382, vol. 47.

Lawrence, R.D., "Lipodystrophy and Hepatomegaly With Diabetes, Lipaemia, and Other Metabolic Disturbances: A Case Throwing New Light on the Action of Insulin," Lancet, 1946, 724-731 and 773-775, vol. 1.

Luyckx, F.H., et al., "Non-Alcoholic Steatohepatitis: Association with Obesity and Insulin Resistance, and Influence of Weight Loss," Diabetes Metab., 2000, 98-106, vol. 26.

Magre, J., et al., "Identification of the Gene Altered in Berardinelli-Seip Congenital Lipodystrophy on Chromosome 11q13," Nat. Genet, 2001, 365-370, vol. 28.

Manton, N.D., et al., "Non-Alcoholic Steatohepatitis in Children and Adolescents," Med. J. Aust, 2000, 476-476, vol. 173.

Mantzoros, C.S., et al., "Editorial: Leptin as a Therapeutic Agent-Trials and Tribulations," J. Clin. Endocrinol. Metab., 2000, 4000-4002, vol. 85.

Moitra, et al., "Life Without Fat: A Transgenic Mouse," Genes. Dev., 1998, 3168-3181, vol. 12.

Montague, C.T., et al, "Congenital Leptin Deficiency is Associated with Severe Early Onset Obesity in Humans," Nature, 1997, 903-908, vol. 387.

Ogawa, Y., et al., "Increased Glucose Metabolism and Insulin Sensitivity in Transgenic Skinny Mice Overexpressing Leptin," Diabetes, 1999, 1822-1829, vol. 48, No. 9.

Pardini, et al., J. Clin. Endocrinol Metab 83: 503-508, 1998.

Pelleymounter, M.A., et al., "Effects of the Obese Gene Product on Body Weight Regulation in ob/ob Mice," Science, 1995, 540-543, vol. 269.

Peters, A.L., "The New Diagnostic Criteria for Diabetes: The Impact of Management of Diabetes and Macrovascular Risk Factors," Am. J. Med., 1998, 15s-19s, vol. 105.

Reitman, M.L., et al., "Lipoatrophy Revisited," Trends Endoctrinol. Metab., 2000, 410-416, vol. 11.

Shimomura, I., et al., "Decreased IRS-2 and Increased SREBP-1c Lead to Mixed Insulin Resistance and Sensitivity in Livers of Lipodystrophic and ob/ob Mice," Mol. Cel., 2000, 77-86, vol. 6.

Shimomura, I., et al., "Insulin Resistance and Diabetes Mellitus in Transgenic Mice Expressing Nuclear SREBP-1c in Adipose Tissue: Model for Congenital Generalized Lipodystrophy," Genes Dev., 1998, 3182-3194, vol. 12.

Shimomura, I., et al., "Leptin Reverses Insulin Resistance and Diabetes Mellitus in Mice with Congenital Lipodystrophy," Nature, 1999, 73-76, vol. 401.

Trygstad, O., et al., "Lipodystrophic Diabetes Treated with Fenfluramine," Int. J. Obesity, 1977, 287-292, vol. 1.

Unger, R.H., et al., "Regulation of Fatty Acid Homeostasis in Cells: Novel Role of Leptin," Proc. Natl. Acad. Sci. USA, 1999, 2327-2332, vol. 96.

Unger, R.H., et al., "Lipotoxicity in the Pathogenesis of Obesity-Dependent NIDDM, Genetic and Clinical Implications," Diabetes, 1995, 863-870, vol. 44.

Van Der Merwe, M. T., "Free Fatty Acids and Insulin Levels: Relationship to Leptin Levels and Body Composition in Various Patient Groups from South Africa," International Journal of Obesity, 1999, 909-917, vol. 23, No. 9.

Yamamuchi, T., et al., "The Fat-Derived Hormone Adiponectin Reverses Insulin Resistance Associated with Both Lipoatrophy and Obesity," Nat. Med., 2001, 941-946, vol. 7.

Zhang, Y., et al., "Positional Cloning of the Mouse Obese Gene and Its Human Homologue," Nature, 1994, 425-432, vol. 372.

Zhang, Y., et al., Correction at Nature, 1995, 479, vol. 374.

Hadigan, Colleen, et al., "Metformin in the Treatment of HIV Lipodystrophy Syndrome," Journal of the American Medical Association, Jul. 26, 2000; 284:4:472-477.

Chen et al., Disappearance of body fat in normal rats induced by adenovirus-mediated leptin gene therapy, PNAS, Vo. 93, pp. 14795-14999, Dec. 1996.

Gavrilova et al., Leptin and diabetes in lipoatrophic mice, Nature, Va. 403, Feb. 24, 2000, pp. 850-851.

Reitman et al., A-ZIP/F1 mice lacking white fat: a model for understanding lipoatrophic diabetes, International Journal of Obesity and Related Metabolic Disorders: Journal of the International Association for the Study of Obesity, Nov. 2000, vol. 24, Suppl4, pp. S114.

Chao et al., (2000), J. Clin. Invest., vol. 06(10): 122 1-1228.

Bolan, C, et al., "Intensive, Long-Term Plasma Exchange Therapy for Severe Hypertriglyceridemia in Acquired Generalized Lipoatrophy," *J. Clin. Endocrin and Metab*. 2002, 87: 380-384.

USE OF LEPTIN TO TREAT METABOLIC ABNORMALITIES ASSOCIATED WITH LIPOATROPHY

CROSS-REFERENCE TO RELATED APPLICATIONS

This is a divisional application of U.S. patent application Ser. No. 11/606,805, filed on Nov. 29, 2006, which is a divisional application of U.S. patent application Ser. No. 10/623, 189, filed on Jul. 18, 2003, now issued as U.S. Pat. No. 7,183,254, which is a continuation application of U.S. patent application Ser. No. 10/279,129 filed on Oct. 22, 2002, now abandoned, which claims the benefit of priority under 35 U.S.C. §119(e) of U.S. Provisional Application No. 60/336, 394, filed on Oct. 22, 2001, the disclosures of which are hereby incorporated by reference in their entirety.

GOVERNMENT INTEREST

The present invention was supported, in part, by funding from the NIH. The government may have certain rights in the invention.

FIELD OF THE INVENTION

The present invention relates to the field of therapeutic use of leptin, leptin analogs, and leptin derivatives for the treatment of human lipoatrophy.

BACKGROUND OF THE INVENTION

All citations herein are incorporated in their entirety by reference. Full citations of the references can be found at the end of the detailed description.

The lipoatrophy (also known as lipodystrophy) syndromes are a heterogeneous group of syndromes characterized by a paucity of adipose or fat tissue. Metabolic abnormalities may also be associated with this condition. These metabolic abnormalities include hypertriglyceridemia and severe insulin resistance usually accompanied by diabetes mellitus (Reitmann et al., 2000). Lipoatrophy in humans may be genetically inherited or acquired. There is more than one genetic form of lipoatrophy. For example, mutations in the gene encoding Lamin A/C (LMNA) has been shown to be associated with the Dunnigan-type familial partial lipodystrophy (FPLD) (Cao et al., 2000). Individuals with Dunnigan's FPLD are born with a normal fat distribution, but at puberty, they develop progressive subcutaneous extremity and truncal fat loss, with sparing of visceral and head and neck adipose tissue. A different chromosomal location (9q34) has also been linked to a disease gene for congenital generalized lipodystrophy (Garg et al., 1999). Congenital generalized lipodystrophy is a recessive disorder characterized by a near complete absence of adipose tissue from birth, insulin resistance, hypertriglyceridemia and acanthosis nigricans.

Some forms of lipoatrophy in humans are acquired. For example, many patients infected with human immunodeficiency virus (HIV) and treated with highly active antiretroviral therapy (HAART) develop a partial lipodystrophy, characterized by loss of subcutaneous fat from the face, extremities and trunk, with increased visceral fat and a 'buffalo hump' similar to that seen in Cushing's syndrome. These patients may also develop metabolic disorders such as insulin resistance and hypertriglyceridemia. Acquired forms of lipoatrophy may also be associated with juvenile dermamyositis and other autoimmune diseases.

Investigations in animal models have demonstrated that these metabolic abnormalities may be associated with fat loss (Gavrilova et al., 2000). But insulin resistance and hypertriglyceridemia that characterize lipoatrophy have been extremely refractory to treatment, even though a variety of approaches have been tried (Garg, 2000). One of these approaches includes treatment with thiazolidinediones, which are PPARγ (peroxisome proliferator activated receptor γ) agonists. While thiazolidinediones are appealing because they promote both adipocyte differentiation and insulin sensitivity, patients receiving thiazolidinediones are usually managed with combination therapy, including high dose insulin, oral hypoglycemic agents (e.g. metformin and thiazolidinediones), and lipid-lowering drugs, (e.g., fibrates and statins). Despite these therapies, patients with generalized lipoatrophy continue to manifest severe hypertriglyceridemia (which causes recurrent attacks of acute pancreatitis), severe hyperglycemia (which poses risk of diabetic retinopathy and nephropathy), and non-alcoholic steatohepatitis (which can result in cirrhosis) (Arioglu et al., 2000). In fact, one member of the thiazolidinediones, troglitazone, was removed from the US market because of its rare but severe hepatotoxicity, leaving two thiazolidinediones (rosiglitazone and pioglitazone) available (Reitmann, et al.). Thus, there exists a need for an alternative treatment to lipoatrophy.

A variety of genetically engineered animal models for lipoatrophy have been developed and tested. These models, however, provide conflicting results as to the sensitivity of these animals to treatment with leptin. For example, in one transgenic mouse model, which expresses a truncated nuclear version of SREBP-1c and mimics the features of congenital generalized lipodystrophy having insulin resistance and markedly low adipose tissue, continuous systemic infusion of leptin overcame the resistance of the mice to insulin (Shimomura et al., 1999). On the other hand, a different transgenic mouse, which expresses the A-ZIP/F-1 gene and characterized by lack of fat tissue, severe resistance to insulin, diabetes, and greatly reduced serum leptin levels, failed to respond to leptin at similar doses and were minimally effective at higher doses (Gavrilova et al., 2000). Any efficacy with leptin also diminished with age of the animal (Id.). Furthermore, although insulin resistance was overcome with leptin in the SREBP-1c transgenic mice, reversal of lipoatrophy was not observed (Shimomura et al.).

Current use of leptin in human therapy has mainly been focused on reducing obesity and its associated metabolic dysfunction (Heymsfield et al. 1999). Patients with absence of leptin due to mutations in the leptin gene are morbidly obese from infancy and have a number of hormonal abnormalities including insulin resistance and hypogonadotropic hypogonadism (Montague et al., 1997). Physiological replacement with recombinant leptin for one year in one of these patients caused significant weight reduction and improvement in the hormonal abnormalities (Farooqi et al., 1999; PCT App. No.: WO 00/20872). These previous studies have not addressed the use of leptin in the context of human lipoatrophy.

SUMMARY OF THE INVENTION

The present invention provides for the use of leptin in treating humans with lipoatrophy and its associated metabolic abnormalities, and provides a method of determining a predisposition to leptin treatment. In one embodiment, human leptin is used in hormone replacement therapy in lipoatrophic patients having reduced serum concentration of leptin. Preferably, recombinant human leptin or leptin analog or derivative is used. Leptin proteins may be administered subcutaneously or systemically, or through any other routes including methods in gene therapy.

In assessing the predisposition of lipoatrophic patient to treatment with leptin, serum concentration of leptin may be determined. Preferably, patients with serum leptin concentration of less than 4 ng/ml, and more preferably, less than 2 ng/ml, and most preferred, less than 0.5 ng/ml, are subjected to leptin treatment. It is also preferred that treatment with leptin be given to female patients with <4 ng/ml of serum leptin concentration and to male patients with <3 ng/ml of serum leptin concentration. More preferably, leptin is given to male patients with <2 ng/ml of serum leptin concentration.

DETAILED DESCRIPTION OF THE PREFERRED EMBODIMENTS

Figure 1A:
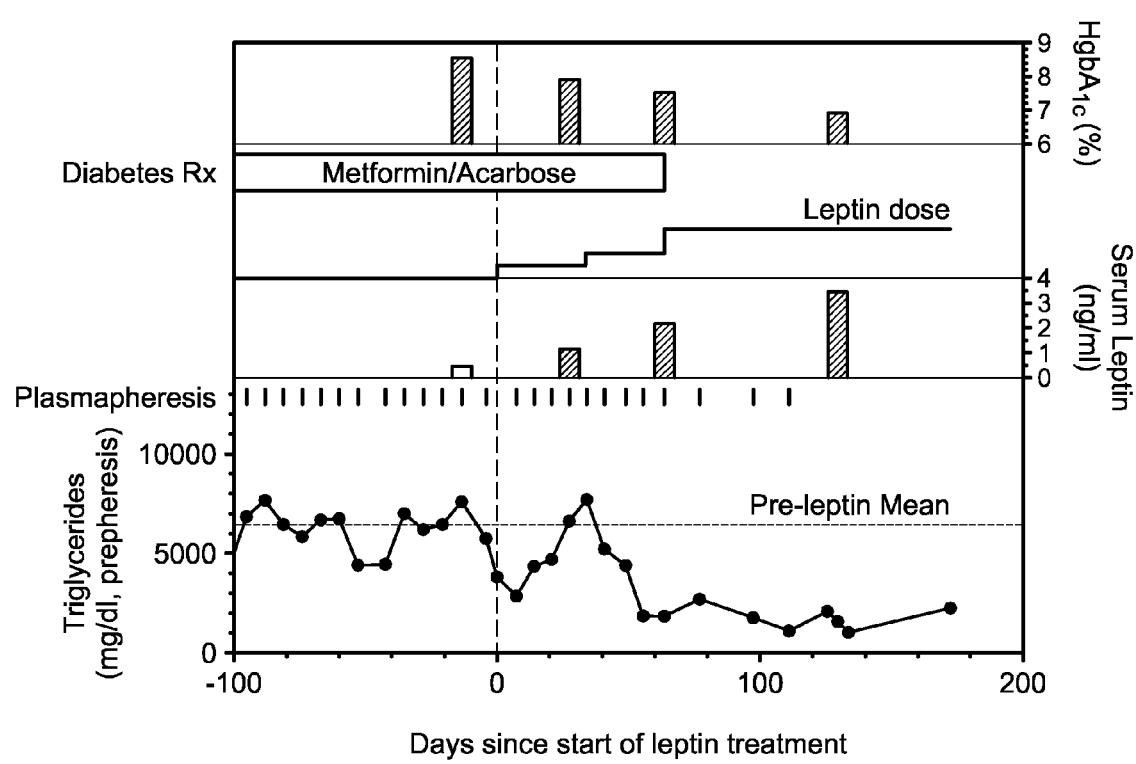
FIG. 1A shows the clinical course of patient NIH-1 with 4 months of leptin therapy. Historical data before leptin therapy (started at Day 0) is presented to demonstrate the severity of metabolic findings. Important milestones of therapy and the improvement in metabolic parameters are shown.

The adipocyte hormone leptin plays a central role in energy homeostasis. It was first discovered in the obese mouse as the missing serum factor that decreased food intake and body weight upon replacement (Zhang et al., 1994; Pelleymounter et al., 1995). Because of these initial observations, much of the earlier therapeutic attempt using this hormone has been in the treatment of obesity. Serum leptin concentrations in the majority of humans with obesity are high, and a state of leptin resistance is thought to exist (Mantzoros et al., 2000). Thus far, the effect of recombinant human leptin has been limited in causing weight loss in obese individuals except in the state of congenital leptin deficiency (Heymsfield et al., 1999; Farooqi et al., 1999).

The present invention provides for the feasibility of using leptin for the treatment of lipoatrophy and its associated metabolic abnormalities in humans such as hyperglycemia, dyslipidemia, hyperlipidemia, hypercholesterolemia, hypertriglyceridemia, atherosclerosis, vascular restenosis, and insulin resistance. Results from studies in HIV patients have shown that decrease in serum concentrations of leptin is closely associated with the onset of acquired lipoatrophy. Furthermore, leptin replacement in lipoatrophic patients dramatically improves glucose and triglyceride metabolism even after all other potential therapies have been extinguished. In all these leptin replacement therapy cases, the baseline serum concentration of leptin was less than 4 ng/ml.

In one severe case of acquired lipoatrophy, the patient (having serum leptin concentration of <0.5 ng/ml) suffered from severe hypertriglyceridemia, diabetes, painful eruptive cutaneous xanthomata, and massive hepatomegaly. Leptin treatment over four months dramatically improved the patient's hypertriglyceridemia and hyperglycemia that allowed for discontinuation of plasmapheresis and other diabetes medications. The improvements were also accompanied by disappearance of the cutaneous xanthomata and the patient's liver volume decreased by 40%. Thus, these data show that leptin replacement therapy may effectively be used to treat acquired or congenital lipoatrophy and its associate metabolic abnormalities in human.

Furthermore, based on these data, it may be extrapolated that patients with less than 4 ng/ml serum concentration for leptin may be a preferred group of patients for replacement therapy with leptin. Leptin levels may be measured using a body fluid, most preferably blood or some portion thereof. Here, serums from individuals were used. Other body fluids may also contain measurable leptin, such as whole blood, cerebral spinal fluid, plasma, and possibly urine. The present measurements of 4 ng of leptin/ml of serum may be correlated to corresponding levels in other body fluids. For example, if whole blood is used, the leptin concentration will be diluted to account for the diluting effect of using unfractionated blood.

One skilled in the art will be able to ascertain effective dosages by administering leptin, leptin analog or leptin derivative and observing the desired therapeutic effect. The goal of replacement therapy is to achieve near physiological concentrations of leptin in the plasma. It is estimated that the physiological replacement dose of leptin is about 0.02 mg per kilogram of body weight per day for males of all ages, about 0.03 mg per kilogram per day for females under 18 years and about 0.04 mg per kilogram per day for adult females. When attempting to achieve near physiological concentrations of leptin, one may, for example, treat a patient with 50 percent of the estimated replacement dose for the first month of treatment, 100 percent of the replacement dose for the second month of treatment, 200 percent of the replacement dose for the third month of treatment, etc. During the course of leptin replacement therapy, one can measure certain biochemical markers to monitor therapeutic effect of the leptin treatment. Glycosylated hemoglobin ($HbA_{1c}$) levels and triglyceride (fasting) levels are among the preferred markers to measure therapeutic effect to monitor the efficacy of leptin treatment.

Alternatively, serum leptin levels can be measured using commercially available immunoassays, as further disclosed in the Examples below. In general, a diagnostic assay for measuring the amount of leptin in the blood (or plasma or serum) may first be used to determine endogenous levels of protein. Such diagnostic tools may be in the form of an antibody assay, such as an antibody sandwich assay. The amount of endogenous leptin is quantified initially, and a baseline is determined. The therapeutic dosages are determined as the quantification of endogenous and exogenous leptin protein (that is, leptin, leptin analog or leptin derivative found within the body, either self-produced or administered). Monitoring the leptin levels of a patient is continued over the course of therapy.

The present invention also provides methods of using pharmaceutical compositions of leptin, leptin analog or leptin derivative. Such pharmaceutical compositions may be for administration for injection, or for oral, pulmonary, nasal, transdermal or other forms of administration. Preferred methods of administering the leptin proteins include subcutaneously, systemically and by gene therapy methods.

In general, pharmaceutical compositions of the present invention comprise effective amounts of leptin, leptin analog or leptin derivative together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used, and this may have the effect of promoting sustained duration in the circulation. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder, such as lyophilized form. Implantable sustained release formulations are also contemplated, as are transdermal formulations.

To aid dissolution of the therapeutic into the aqueous environment a surfactant might be added as a wetting agent. Surfactants may include anionic detergents such as sodium butyl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives that potentially enhance uptake of the leptin, leptin analog or leptin derivative protein are for instance the fatty acids oleic acid, linoleic acid and linolenic acid.

Controlled release formulation may be desirable. The leptin, leptin analog or leptin derivative protein could be incorporated into an inert matrix which permits release by either diffusion or leaching mechanisms e.g., gums. Slowly degenerating matrices may also be incorporated into the formulation, e.g., alginates, polysaccharides. Another form of a controlled release of this therapeutic is by a method based on the Oros therapeutic system (Alza Corp.), i.e., the leptin, leptin analog or leptin derivative protein is enclosed in a semi-permeable membrane, which allows water to enter and push the protein out through a single small opening due to osmotic effects. Some enteric coatings also have a delayed release effect.

Further, improved kits for determining the predisposition of a human patient with lipoatrophy to respond to treatment with leptin, leptin analog or leptin derivative are contemplated by the present invention. In one aspect, an improved kit may provide means for determining whether the leptin level of the patient prior to said leptin treatment is less than or equal to approximately 4 ng/ml. In a related aspect, an improved kit may consider the gender of a patient when determining a leptin level in the patient prior to said leptin treatment. Then, the kit may provide means for determining whether the leptin level of the patient prior to said leptin treatment is less than or equal to approximately 2 ng/ml if the patient is male, or less than or equal to approximately 4 ng/ml if the patient is female. Preferably, the kit comprises instructions for use. The kit may also comprise reagents, tubes, packaging, and/or other reaction components.

The following descriptions are provided only as examples and should not be understood to be limiting on the claims. Based on the description, a person skilled in the art may make modification and changes to the preferred embodiments, which do not depart from the scope of the invention.

EXAMPLE I

The following example shows that the development oil-RV-associated lipoatrophy syndrome (HIV-LS) may be influenced by reduced leptin in the serum, which contributes to the accumulation, loss or redistribution of body fat.

In particular, a study was conducted for the purpose of determining whether the lipoatrophy phenotype in HIV-LS is associated with changes in serum leptin following initiation of highly active antiretroviral therapy (HAART). This study included one hundred forty six (146) HIV positive men whose serum leptin concentrations were compared before and after HAART. By physical examination, the men were assessed and stratified into the two major phenotypes: lipoatrophy alone and lipoatrophy with central fat gain ("mixed" HIV-LS).

Out of the 146 men, forty-two (42/146) men were found to have moderate or severe lipoatrophy or lipohypertrophy in more than one body area following HAART. Twenty-seven of the 146 (27/146) had lipoatrophy alone and fifteen (15/146) had "mixed" changes after HAART. Thirty-nine out of the 146 (39/146) did not have body habitus changes and these patients served as controls. Generally, the men with HIV-LS were older and had longer use of protease inhibitors. They also had lower baseline CD4 counts and had lost an average of 4 kg body weight from baseline.

Before HAART, median baseline leptin levels for both the lipoatrophy and "mixed" groups were 3.6 ng/ml and median leptin level for the control was 4.1 ng/ml. In those who developed lipoatrophy alone after HAART, serum leptin concentration decreased significantly from 3.6 to 2.8 ng/ml (Wilcoxon p=0.006). On the other hand, serum leptin levels remained stable in both the "mixed" HIV-LS group (4.0 ng/ml) [p=NS] and in the 39 HIV positive controls who did not develop HIV-LS (3.7 ng/ml) [p=NS].

These data suggest that a reduced leptin level following the highly active antiretroviral therapy in HIV positive patients may contribute to the development of lipoatrophy syndrome.

EXAMPLE II

To determine the efficacy of using leptin to treat lipoatrophy in humans, leptin replacement therapy was also conducted in nine female patients who have been diagnosed with various forms of lipoatrophy. The patients of this study were referred by multiple physicians in the United States and in Europe. To be eligible, the patients were required to have low levels (defined as serum leptin concentration of <3.0 ng/ml in males and <4.0 ng/ml in females) in association with lipodystrophy, and at least one of the following metabolic abnormalities: (1) Presence of diabetes mellitus by American Diabetes Association criteria (See Peters et al., 1998); (2) fasting serum triglyceride concentrations >200 mg/dL; and/or (3) fasting serum insulin concentrations >30 μU/ml. The diagnosis of lipodystrophy was based on clinical grounds well known to one ordinary skilled in the art.

Table 1 summarizes the baseline clinical characteristics of the patients treated in the study.

TABLE 1

Characteristics of Patients

| Patient | Age/Sex/Type | Lipid-Lowering Therapy | Fasting Insulin[1] (μU/mL) | Leptin[2] (ng/mL) | RMR[3] (kcal/day) | Total Fat[4] (%) |
|---|---|---|---|---|---|---|
| NIH-1 | 17/F Acquired Generalized | Fenofibrate Atorvastatin Orlistat, Weekly Plasmapharesis | 31.2 | <0.5 | 2010 | 7 |
| NIH-2 | 17/F Congenital Generalized | None | 334 | 1.0 | 2030 | 17 |
| NIH-3 | 27/F Acquired Generalized | None | 19 | 0.7 | 1570 | 18 |
| NIH-4 | 17/F Congenital Generalized | None | 211 | 1.1 | 2480 | 17 |
| NIH-5 | 15/F Congenital Generalized | None | 115 | 0.8 | 2670 | 15 |
| NIH-6 | 37/F Congenital Generalized | None | 25 | 0.6 | 1370 | 15 |
| NIH-7 | 42/F Familial Partial | Gemfibrozil | 40.3 | 3.6 | 1980 | 26 |
| UTSW-1 | 31/F Congenital Generalized | Fenofibrate | 61.5 | 0.7 | 1702 | 8 |
| UTSW-2[5] | 33/F Acquired Generalized | Gemfibrozil | 12.3 | 2.4 | 1497 | 14 |

[1] Fasting insulin, conversion factor to pmol/L: 7.15X (note that some patients are on exogenous insulin therapy)
[2] Conversion factor to nmol/mL: 0/08X
[3] Residing metabolic rate
[4] Obtained by measurements using dual-energy X-ray absorbtiometry where the measurements are 7-8% higher than underwater weighing technique.
[5] Non-diabetic patient All nine patients recruited into the study were females. Though the study was open to both genders, females tend to be recognized earlier and more frequently. Five of the nine patients had congenital generalized lipodystrophy or the Seip-Beradinelli Syndrome. This diagnosis was established with evidence of generalized fat loss since birth, in association with other clinical criteria (Online Mendelian Inheritance in Man, OMIM #269700; Garg et al., 1992). Three patients appeared to have acquired generalized lipodystrophy with a history of apparent fat loss in childhood. One of these patients (UTSW-2) developed generalized lipodystrophy with juvenile dermatomyositis. Another patient (NIH-7) had Dunnigan's familial partial lipodystrophy (OMIM #151660; Garg, 1999; and Can et al., 2000).

Study Design

The study was designed as a prospective open-label study at the Diabetes Branch of National Institute of Diabetes, Digestive and Kidney Diseases (NIDDK), and at the University of Texas Southwestern (UT Southwestern) Medical Center at Dallas. Amgen Inc. (Thousand Oaks, Calif.) provided recombinant methionyl human leptin (recombinant leptin) for the trial. Response of each patient was compared to her baseline state. Because of the rarity of lipoatrophy syndromes and the variability of the clinical features, it was not feasible to include a randomized placebo-treated control group. The institutional review boards of the NIDDK and University of Texas Southwestern Medical Center approved the study. Informed written consent was obtained from the patient or the legal guardian.

Patients were evaluated as in-patients at the Clinical Center of the National Institutes of Health and at the General Clinical Research Center of the University of Texas Southwestern Medical Center before treatment and again after 1, 2 and 4 months of leptin therapy. All patients were on stable doses of concomitant medications for at least 6 weeks before starting leptin. During the study, hypoglycemic drugs were tapered or discontinued as needed.

The goal in this study was to achieve near-physiological concentrations of leptin in the plasma. The physiological replacement dose was estimated to be 0.02 mg/kg/day for males of all ages, 0.03 mg/kg/day for females under 18 years and 0.04 mg/kg/day for adult females. Recombinant leptin was administered subcutaneously every 12 hours. It is important to note that the replacement dose is approximately one tenth of the dose most commonly used in obesity trials. Patients were treated with 50% of the replacement dose for the first month, 100% replacement dose the next month and 200% replacement dose for the following two months. The primary end-points to determine efficacy of recombinant leptin were determined as Hemoglobin $A_{1c}$ and fasting serum triglyceride levels.

Biochemical Analyses

Serum glucose and triglyceride levels were determined by standard methods using automated Hitachi equipment (Boehringer Mannheim, Indianapolis, Ind.) and using Beckman Instrument (Beckman, Calif.). Hemoglobin $A_{1c}$ was determined by ion-exchange high-pressure liquid chromatography (Bio-Rad Laboratories Inc., Hercules, Calif.). Serum free fatty acid (FFA) levels were determined with a commercial kit (Wako, Richmond, Va.). Serum insulin levels were determined by immunoassays using reagents provided by Abbott Imx Instrument (Abbott Park, Ill.) and a commercial kit (Linco Research, Inc., St. Charles, Mo.). Serum leptin levels were determined by immunoassays using a commercial kit (Linco Research, Inc. St. Charles, Mo.).

Procedures

Resting energy expenditure was measured using Deltatrac Equipment (Sensormedics, Yorba Linda, Calif.). The test was performed after an overnight fast for more than 8 hours in resting patients upon awakening between 6 and 8 AM. Oral glucose tolerance test was performed after an overnight fast using 75 grams of dextrose. Serum glucose was measured at −10, 0, 30, 60, 90, 120 and 180 minutes of the glucose load.

A high-dose insulin tolerance test was performed using 0.2 IU/kg regular insulin to assess insulin sensitivity. Insulin was administered intravenously after an overnight fast. Samples for glucose were collected at −10, 0, 5, 10, 15, 20 and 30 minutes of insulin administration. K constant (the rate of glucose disappearance as a reflection of total body insulin sensitivity) was calculated as the rate constant for the fall in blood glucose after intravenous insulin using first order kinetics (Harrision et al., 1976).

Body fat was determined using dual energy x-ray absorptiometer (DEXA, Hologic QDR 4500) (Hologic, Inc., Bedford, Mass.) (Lambrinoudaki et al., 1998). Axial T1 weighted MR scans of the liver were obtained on a 1.5 tesla scanner (General Electric Medical Systems, Milwaukee) (Abate et al., 1994). Liver volumes were calculated using the MEDx image analysis software package (Sensor Systems, Inc., Sterling, Va.), on a Sun workstation. By placing a seed point for an edge following algorithm, tracings of the outer margins of the liver were made on individual contiguous slices. The liver volumes were then computed based on the pixel area and slice thickness. Subjects participating at the NIH-site were asked to report their food intake in the last 3 days at baseline and at 4-months to calculate estimated daily food intake (Feskanich et al., 1993).

Statistical Analyses

Measurements are presented as mean±SEM. To compare study variables during various study periods, repeated measures analysis of variance was used. Skewed data such as the triglyceride concentrations and the calculated K constants were log-transformed. Paired t-test was employed to compare baseline data with various time points wherever applicable. Plasma glucose concentration during the oral glucose tolerance test were compared using a 2-factor analysis of variance with study period and time during the test modeled as repeated factors. Ninety-five percent confidence intervals of the differences between the means were derived from the analysis of variance and for the differences between the means (Hanh et al., 1991). Changes were considered statistically significant for $p<0.05$. No adjustments for simultaneous comparisons were made for statistical analyses of specific a priori hypotheses.

Results

Baseline Patient Characteristics

Eight of nine patients in the study were diabetic and all were hyperlipidemic (Table 1). All diabetic patients received pharmacotherapy prior to the study (Table 1 and 2) and 4 patients received pharmacotherapy for lipid management (Table 1). The average $HbA_{1c}$ of the diabetic patients was 9.1±0.5% (normal: <5.6%). The mean triglyceride levels were elevated at 1405 mg/dL (range: 322-7,420 mg/dL; normal range: 35-155 mg/dL) [16 mmol/L, range: 3.6-8.7 mmol/L]. Free fatty acid (FFA) levels were increased about 3-fold from the upper limit of normal (1540±407 μmol/L; normal: 350-550 μmol/L). Six of the seven NIH patients had fatty liver on ultrasound and enlarged livers on physical exam. Three of the patients underwent liver biopsies and two of the three were diagnosed with non-alcoholic steatohepatitis based on histopathological criteria (Manton et al., 2000; Berasain et al., 2000; Luyckx, et al., 2000).

The mean serum leptin concentration was 1.3±0.3 ng/mL at baseline (Table 1) which increased with therapy to 2.3±0.5 ng/mL at the end of the first month, 5.5±1.2 ng/mL at the end of the second month, and 11.1±2.5 ng/mL at the end of the fourth month. Therefore, recombinant leptin administration at the doses used in this study resulted in approximately normal serum leptin levels in these patients.

Effect of Leptin on the First Patient: A Case Example (FIG. 1)

Figure 1B:
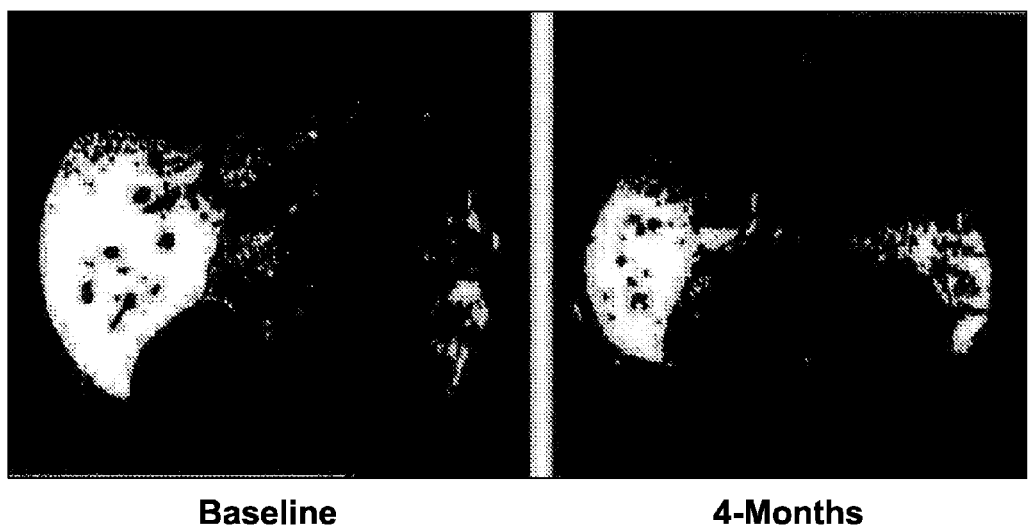
FIG. 1B depicts a T1-weighted axial magnetic resonance imaging of patient NIH-1 at the level of L4 at baseline and at 4-months of leptin therapy. Note the decrease in liver size, and the consequent changes in position of the kidneys and midline structures.

The first patient treated in the study (NIH-1) is the most severely affected and her course is instructive in showing the dramatic effect of leptin replacement in this population even after all other potential therapies have been extinguished. This patient was born healthy, but experienced fat loss between age 10 and 12. She developed severe hypertriglyceridemia at age 13 and diabetes at age 14. She was presented to the NIH Clinical Center at age 15 with triglyceride levels consistently >10,000 mg/dL (>113 nmol/L) and diabetes with $HbA_{1c}$ of 9.5%. She had painful eruptive cutaneous xanthomata scattered throughout the body and massive hepatomegaly extending to the pelvic brim. Weekly plasmapheresis therapy and Orlistat were added to alleviate hypertriglyceridemia (FIG. 1A) (Bolan et al.). Other remarkable clinical features included a voracious appetite (she reported eating in excess of 3200 kcal/day) and a greatly elevated resting metabolic rate at 2010 kcal/day, 180% of predicted. Over a four-month period, recombinant leptin caused a marked progressive improvement in hypertriglyceridemia and hyperglycemia that allowed for discontinuation of plasmapheresis and diabetes medications (FIG. 1A). The improvements in metabolic parameters were accompanied by disappearance of cutaneous xanthomata. In addition, her liver volume decreased by 40% (from 4213 mL at baseline to 2644 mL at 4 months, shown in FIG. 1B).

Leptin Improved Metabolic Control in all Diabetic Lipoatrophic Patients

Figure 2:
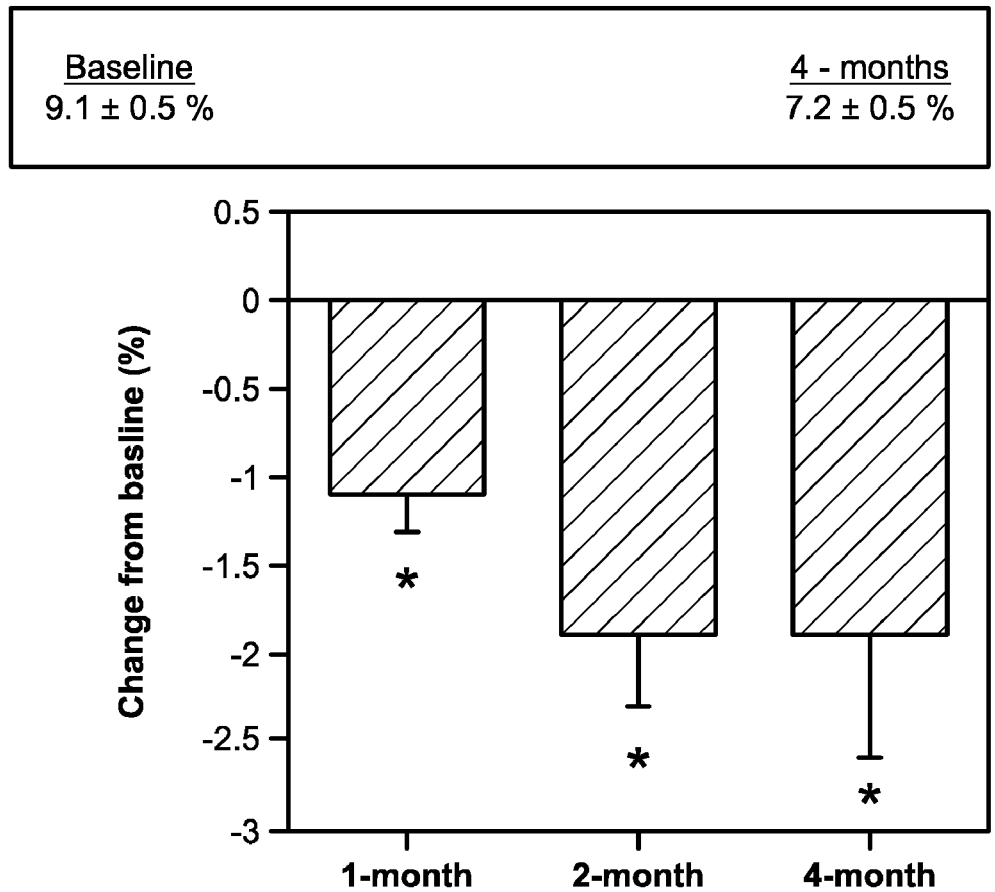
FIG. 2 shows that leptin decreases $HbA_{1c}$ in the diabetic patients (n=8). Data are presented as mean changes and error bars indicate 95% Confidence Interval. The baseline and 4-month value±SEM (standard error of the mean) are also shown. *p<0.001.

Prior to the initiation of leptin therapy, the eight diabetic lipoatrophic patients bad poor metabolic control. With four months of leptin replacement therapy, $HbA_{1c}$ decreased by a mean of 1.9 percentage points (95% CI, 1.1 to 2.7%, p=0.0012) (FIG. 2). Individual responses of patients are shown in Table 3. It is notable that glycemic control improved despite decreasing or discontinuing baseline anti-diabetes therapy (Table 2).

TABLE 2

Changes in hypoglycemic therapy during the study

| Patient | Hypoglycemic therapy during baseline period | Hypoglycemic therapy at 4-months of therapy |
|---|---|---|
| NIH-1 | Metformin (500 mg bid) | None |
|  | Acarbose (50 mg tid) |  |
| NIH-2 | Insulin (800 U/day) | None |
| NIH-3 | Insulin (40 U/day) | None |
|  | Metformin (500 mg tid) |  |
| NIH-4 | Insulin (1200 U/day) | None |
| NIH-5 | Insulin (3000 U/day) | None |
| NIE-6 | Metaformin (500 mg tid) | None |
| NIH-7 | Insulin (200 U/day) | Insulin (60 U/day) |
|  | Proglitazone (5 mg qd) |  |
| UTSW-1 | Insulin (700 U/day) Insulin | (300 U/day) |
| UTSW-2 Nondiabetic patient | None | None |

Figure 3A:
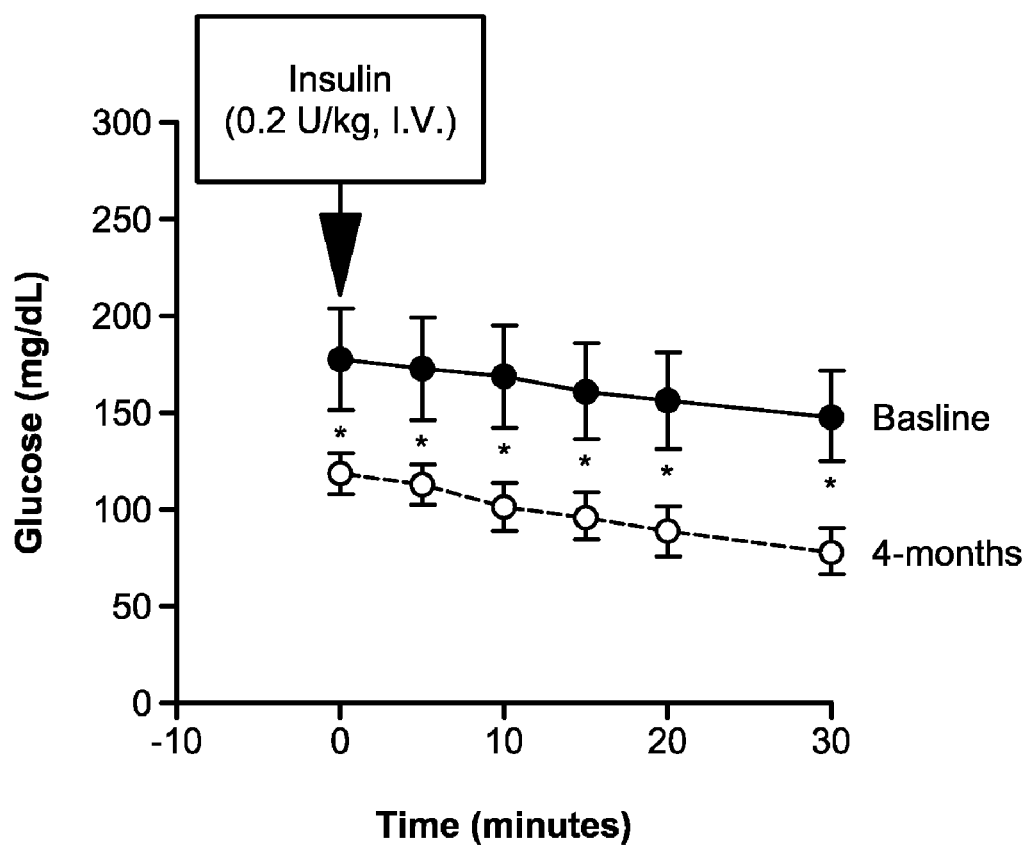
FIG. 3 shows that leptin improves the glucose curve during both insulin tolerance and oral glucose tolerance (n=9). Panel A: Plasma glucose in response to 0.2 U·kg IV insulin before (closed circles and solid line) and 4-months after (open circles and dotted line) leptin therapy. Error bars indicate SEM *p<0.02. Panel B: Plasma glucose in response to 75-gram oral glucose before (closed circles and solid line) and 4-months after (open circles and dotted line) leptin therapy. Error bars indicate SEM. *p<0.01.
Figure 3B:
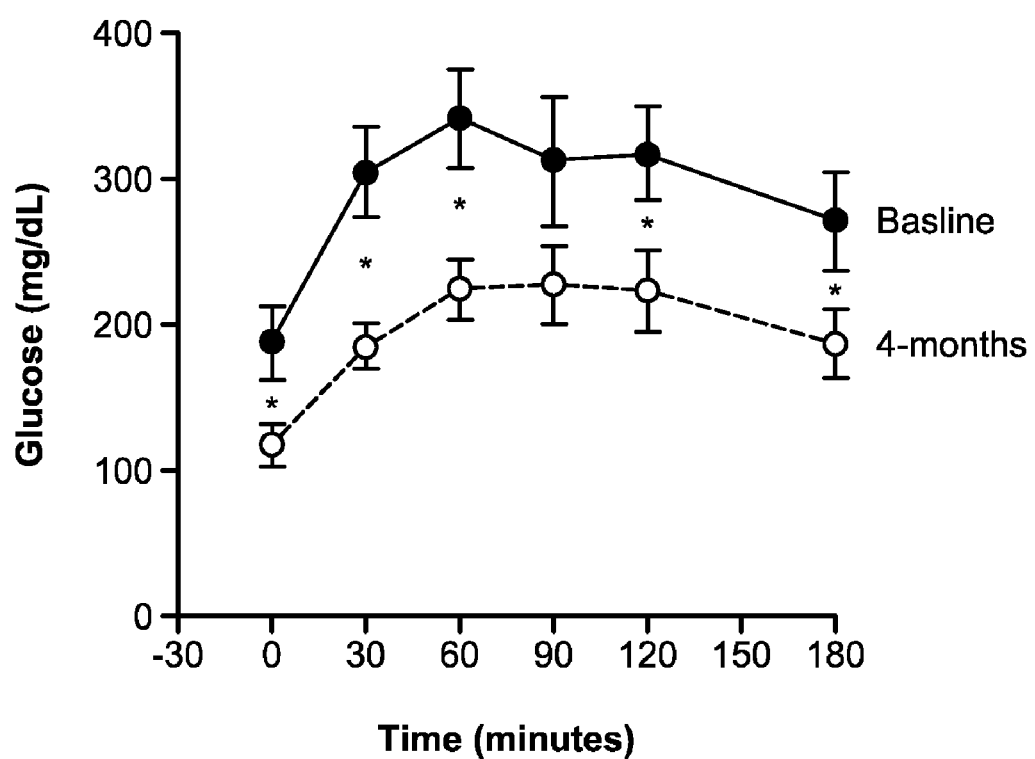

The plasma glucose levels during the insulin tolerance test showed significant improvement at the end of 4 months compared to the baseline (FIG. 3A). The K-value (rate of glucose disappearance) increased from 0.0071±0.0012 to 0.0169±0.0039 indicating improvement of whole-body insulin sensitivity (p=0.035). Further, the oral glucose tolerance was also significantly improved compared to baseline (FIG. 3B).

Figure 4:
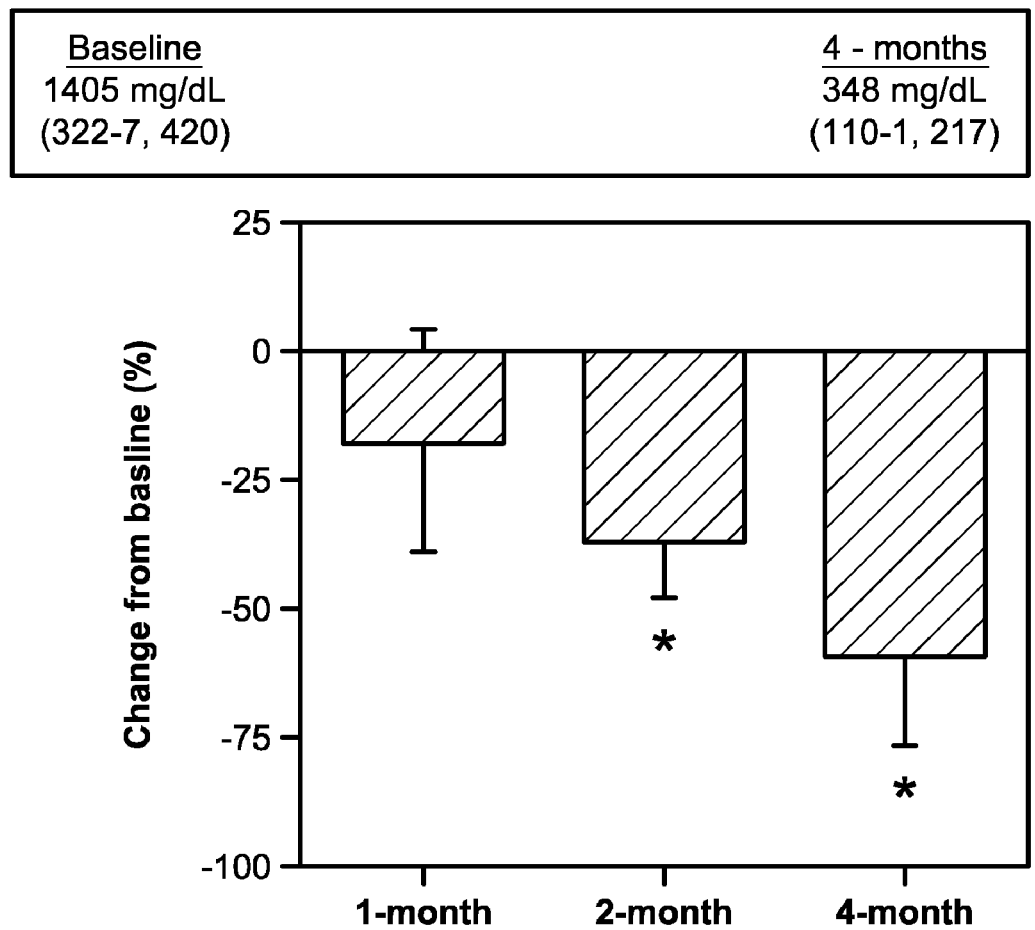
FIG. 4 shows that leptin decreases triglycerides. Data are presented as mean change from baseline and error bars represent 95% Confidence Interval. The mean baseline and 4-month values with observed ranges are also shown. Note that data are skewed and do not follow a normal distribution. *p<0.001.

At the end of four months of recombinant leptin therapy, the fasting triglyceride levels fell by 60% (CI, 43 to 77%, p<0.001, FIG. 4). During this same period, fasting free fatty acids fell from 1540±407 μmol/L to 790±164 μmol/L (p=0.045). Individual responses are shown in Table 3.

TABLE 3

Patients' metabolic parameters during different stages of therapy

| Patients | HbA$_{IC}$ (%) | | | | Triglycerides[1] (mg/dL) Month[3] | | | | Free fatty acids[2] (pmol/L) | | | |
|---|---|---|---|---|---|---|---|---|---|---|---|---|
| | 0 | 1 | 2 | 4 | 0 | 1 | 2 | 4 | 0 | 1 | 2 | 4 |
| NIH-1 | 8.6 | 7.6 | 7.4 | 7.0 | 7420 | 6440 | 1632 | 1214 | 3977 | 3517 | 2216 | 1701 |
| NIH-2[4] | 9.8 | 8.3 | 7.4 | 10.0 | 633 | 523 | 471 | 405 | 2922 | 1452 | 1372 | 1244 |
| NIH-3 | 9.3 | 7.8 | 8.4 | 7.9 | 450 | 579 | 233 | 281 | 919 | 368 | 451 | 454 |
| NIH-4 | 7.6 | 6.7 | 6.1 | 5.0 | 322 | 232 | 160 | 106 | 1838 | 1388 | 866 | 446 |
| NIH-5 | 9.5 | 9.4 | 6.5 | 6.1 | 913 | 427 | 143 | 123 | 1066 | 1842 | 723 | 629 |
| NIH-6 | 9.2 | 8.6 | 7.2 | 7.4 | 663 | 355 | 242 | 303 | 1672 | 1367 | 1315 | 428 |
| NIH-7 | 9.5 | 8.4 | 7.4 | 6.6 | 802 | 366 | 295 | 215 | 384 | 315 | 306 | 345 |
| UTSW-1 | 9.5 | 8.1 | 7.5 | 7.3 | 995 | 827 | 383 | 192 | 560 | 360 | 525 | 560 |
| UTSW-2[5] | 5.4 | 4.8 | 5.0 | 5.1 | 447 | 656 | 276 | 424 | 520 | 630 | 1690 | 1310 |

[1] Fasting plasma triglyceride levels, conversion factor to mmol/L: 0.1129X, normal 35-155 mg/dL
[2] Fasting free fatty acid levels, normal 135-550 pmol/L
[3] Month of therapy, 0 refers to baseline evaluation period
[4] This patient had noncompliance between 3$^{rd}$ and 4$^{th}$ months of therapy. After two months of strict compliance as documented by vials of medication used, the reported parameters were respectively: 7.3%, 283 mg/dL and 799 pmol/L
[5] Non-diabetic patient Changes in Liver Volume, and Liver Function Tests Baseline mean liver volume was 3097±391 mL (about 4-fold elevated compared to age and sex-matched normal weight individuals). Leptin decreased the liver volume by an average of 28% (CI, 20 to 36%) from baseline. The mean decrease in liver volume was 987 mL (CI, 546 to 1428 mL, p=0.0024). The improvement in liver size was associated with improvement in liver function tests. Baseline alanine-transaminase concentrations decreased from 66±16 U/L to 24±4 U/L at the end of 4 months (p=0.023). Likewise, serum aspartic-transaminase concentrations were 53±12 U/L at baseline and 21±2 U/L at the end of 4-months (p=0.03).

Changes in Energy Balance

Self-reported daily caloric intake was greatly reduced from a baseline of 2680±250 kcal/day to 1600±150 kcal/day (p=0.005, n=7). There was a parallel decease in the measured resting metabolic rate 1920±150 kcal/day to 1580±80 kcal/day (p=0.003, n=9).

All but one (NIH-3) subject had weight loss at the end of 4 months. The mean weight loss was 3.6*0.9 kg with a range between −1.7 and 7.3 kg. An important fraction of weight loss (50-65%) can be attributed to loss of liver weight.

Tolerability and Adverse Events

No skin reactions at injection sites were reported or observed. There were no trends towards adverse effects on routine biochemical or hematological parameters. Patients NIH-1 had a severe episode of nausea and vomiting after the first dose. Patient NIH-6 had exacerbation of hypertension after the second dose associated with flushing.

Patient NIH-7 was hospitalized due to streptococcus infection during the third month of therapy. None of these events recurred with continued therapy.

Discussion

In this study, leptin replacement led to clear and dramatic metabolic benefits in a group of patients with lipodystrophy and leptin deficiency. During the study, replacement with recombinant leptin resulted in 1.9 percentage point improvement in HbA$_{1c}$, which is predicted to decrease the relative risks to develop retinopathy by ~22% in the diabetic population (UK PDS, 1998). Furthermore, triglyceride levels fell by 60%, which is predicted to decrease the relative risk for cardiovascular events in the general population by 35-65% (Kreisberg, 1998; Garg, 2000)

These results provide a novel insight into the mechanisms of action of leptin. Leptin signal appears to regulate total body insulin sensitivity and triglyceride levels in addition to its known role in the control of energy homeostasis. This study is the first evidence that leptin functions as an insulin-sensitizing and insulin-sparing agent in vivo in humans.

Although a randomized study design was not employed, the weight of evidence suggests that the improved metabolic control was caused by leptin rather than improved compliance associated with participation in a study. First, the magnitude and reproducibility of the improvement of are most consistent with a drug effect rather than a placebo effect. Despite the heterogeneity of the patients included in our study, we observed a uniform improvement in metabolic control in all the diabetic patients. There was evidence of noncompliance in patient NIH-2, explaining the worsening of her HbA$_{1c}$ between 2 and 4 months that was corrected with prolonged therapy (Table 3). This patient-improved drug withdrawal is strong evidence that the effect on improved HbA$_{1c}$ levels is due to leptin administration.

Effect of Leptin on Food Intake

It is recognized that limiting caloric intake in lipoatrophic diabetes improves glucose and lipid abnormalities (Trygstad et al., 1977). However, patients have difficulty complying with meal limitations due to their appetite. Leptin clearly reduced food intake in these patients. A limited study was carried out with Patient NIH-1 to determine the contribution of decreased food intake on the metabolic parameters. In the hospital, she underwent 9 days of leptin withdrawal with caloric intake clamped at pre-withdrawal levels. Despite being on a steady diet, her fasting insulin, triglyceride and glucose concentrations increased within 48 hours. These observations indicate that leptin has effects on insulin sensitivity and triglyceride metabolism independent of its effects on food intake. Similar data using pair-feeding experiments in lipoatrophic mice with or without leptin administration have been reported (Shimomura et al., 1999; Ebihara et al., 2001).

Correlation with Mouse Models

The various mouse models of lipoatrophy suggested that the absence of adipose tissue is the cause of insulin resistance in this syndrome (Burant et al., 1997; Moitra et al., 1998; Shimomura et al., 2000). The demonstration that transplantation of adipose tissue into lipoatrophic mice dramatically ameliorates insulin resistance and improves metabolic control provides strong support for this hypothesis (Gavrilova et al., 2000). However, it remained unclear why adipose tissue was required to maintain whole body insulin sensitivity. The observations and the results discussed above, together with Shimomura et al supra, suggest that the majority of the regulatory action of adipose tissue on whole body insulin sensitivity act through leptin.

Possible mechanism of how leptin regulates both insulin sensitivity and lipid metabolism may be based on SREBP1c, a transcription factor stimulating lipogenesis. In the liver, SREBP1c is upregulated by hyperinsulinemia seen in lipoatrophy. Leptin deficiency and hyperinsulinemia cause downregulation of insulin-receptor substrate, IRS-2, impairing insulin action and increasing hepatic glucose output. The increased lipogenesis and hepatic glucose output create a vicious cycle. Increased tissue lipid levels are associated with decreased whole body insulin sensitivity and thus more hepatic glucose output. Replacement of leptin is shown to correct this vicious cycle. While the rate of triglyceride synthesis was not studied in humans with lipoatrophy, the indirect calorimetric studies provide some evidence that lipogenesis may in fact be dysregulated (Arioglu et al., 2000). Another observation was the decline in resting energy expenditure in the patients treated in this study. This may be due to decreased food intake resulting in reduced diet-induced thermogenesis.

Leptin: An Anti-Steatosis Hormone

It has been reported that leptin administration in Zucker rats leads to correction of steatosis in a variety of organs that act as lipid accumulation sites; such as the islet cells of the liver or heart cells (Unger, 1995; Unger et al., 1999). The lipid accumulation outside of the adipocytes may be a spill over phenomenon resulting from the adipocytes having reached maximum capacity to store triglycerides. In lipodystrophy, these organs are the only sites that can store lipids. Leptin treatment in mice with lipodystrophy causes a dramatic fall in hepatic triglyceride stores. In parallel, leptin therapy in humans with lipodystrophy causes a remarkable, highly significant reduction in liver volumes.

Timing for Leptin Replacement

The concept that adipose tissue is an endocrine organ was strongly supported by the discovery of leptin. Leptin has effects, both direct and/or indirect, on the key organs of metabolism, including the brain, liver, muscle, fat and pancreas. Leptin certainly is not the only circulating adipocyte signal. For example, another adipocyte hormone is adipocyte specific complement related protein (ACRP) 30/Adiponectin/AdipoQ which seems to be important in inducing fat oxidation in the muscle and liver (Yamauchi et al., 2001; Fruebis et al., 2001; Berg et al., 2001). Lack of adipocytes should result in deficiency of all fat-derived signals known and yet to be discovered, thus contributing to many of the abnormalities seen in syndromes characterized by absence of fat. This study is the first human study looking at the metabolic efficacy of replacing a fat-derived hormone in a state of fat deficiency. It appears that leptin deficiency is the major contributor (but probably not the only one) to the metabolic abnormalities seen in association with lipoatrophy. As such, this study underscores an important reason to consider leptin replacement therapy in humans; namely severe lipodystrophy.

EXAMPLE III

The amino acid sequence for mature, recombinant methionyl human leptin is presented herein as SEQ ID NO. 1, where the first amino acid of the mature protein is valine (at position 1) and a methionyl residue is located at position −1 (herein called rHu-Leptin 1-146, SEQ ID No. 1).

```
V P I Q K V Q D D T K T L I K T I V
T R I N D I S H T Q S V S S K Q K V T G
L D F I P G L H P I L T L S K M D Q T L
A V Y Q Q I L T S M P S R N V I Q I S N
D L E N L R D L L H V L A F S K S C H L
P W A S G L E T L D S L G Q V L E A S G
Y S T E V V A L S R L Q G S L Q D M L W
Q L D L S P G C
```

Alternatively, one may use a natural variant of human leptin, which has 145 amino acids, and, as compared to rHu-Leptin 1-146, has a glutamine absent at position 28, presented below (herein called rHu-Leptin 1-145, SEQ ID NO. 2, wherein the blank ("*") indicates no amino acid).

```
V P I Q K V Q D D T K T L I K T I V
T R I N D I S H T * S V S S K Q K V T G
L D F I P G L H P I L T L S K M D Q T L
A V Y Q Q I L T S M P S R N V I Q I S N
D L E N L R D L L H V L A F S K S C H L
P W A S G L E T L D S L G G V L E A S G
Y S T E V V A L S R L Q G S L Q D M L W
Q L D L S P O C
```

Other examples of leptin proteins, analogs, derivatives, preparations, formulations, pharmaceutical composition, doses, and administration routes have previously been described in the following PCT Applications and are hereby incorporated by reference as if fully set forth herein. PCT International Publication Number WO 96/05309; WO 96/40912; WO 97/06816; WO 00/20872; WO 97/18833; WO 97/38014; WO 98/08512 and WO 98/28427.

Leptin proteins, analogs and related molecules are also reported in the following publications; however, no representation is made with regard to the activity of any composition reported.

U.S. Pat. Nos. 5,521,283; 5,525,705; 5,532,336; 5,552,522; 5,552,523; 5,552,524; 5,554,727; 5,559,208; 5,563,243; 5,563,244; 5,563,245; 5,567,678; 5,567,803; 5,569,743; 5569,744; 5,574,133; 5,580,954; 5,594,101; 5,594,104; 5,605,886; 5,614,379; 5,691,309; 5,719,266 (Eli Lilly and Company);

PCT WO96/23513; WO96/23514; WO96/23515; WO96/23516; WO96/23517; WO96/23518; WO96/23519; WO96/34111; WO 96 37517; WO96/27385; WP 97/00886; EP 725078; EP 725079; EP 744408; EP 745610; EP 835879 (Eli Lilly and Company);

PCT WO96/22308 (Zymogenetics);

PCT WO96/31526 (Amylin Pharmaceuticals, Inc.)

PCT WO96/34885; WO 97/46585 (SmithKline Beecham, PLC);

PCT WO 96/35787 (Chiron Corporation);

PCT WO97/16550 (Bristol-Myers Squibb);

PCT WO 97/20933 (Schering Corporation)

EP 736599 (Takeda);
EP 741187 (F. Hoffman La Roche).

To the extent these references provide for useful leptin proteins or analogs, or associated compositions or methods, such compositions and/or methods may be used in conjunction with the present methods. With the above provisos, these publications are herein incorporated by reference.

EXAMPLE IV

A standard enzyme-linked immunosorbent assay (ELISA) may be used to determine leptin levels in the serum of lipoatrophic patients according to one embodiment of the present invention. The ELISA method may use a purified rat monoclonal anti-rmetHu-Leptin antibody for capturing leptin from serum. Affinity purified rabbit anti-rmetHu-leptin polyclonal antibody conjugated to horseradish peroxidase may also be used to detect captured leptin. The limit of detection of the said assay using these antibodies may be in the range of 0.5-0.8 ng/ml. Although certain antibodies may have been used, preferred antibodies are those which specifically react with native human leptin, and are sensitive to detect leptin quantities of equal to or below 5 ng/ml serum.

Preferably, the timing for determining the baseline leptin levels in a patient is after an 8-12 hour fast such as during morning hours. Baseline leptin levels may not be confounded by raising levels, such as after a meal, or due to sleep cycle rise in leptin seen in most individuals (e.g., 3:00 a.m. rise in leptin levels). Such baseline levels may be used, such as observation of nocturnal elevation of leptin levels, but those levels should be compared against similar levels in similarly situated patients.

Based on the above data, a method of determining predisposition of lipoatrophic patients to treatment with leptin can be performed by determining the leptin level corresponding to the serum leptin concentration and ascertaining that the serum leptin concentration is about 4 ng/ml or less.

REFERENCES CITED

1. Zhang Y, Proenca R, Maffei M, Barone M, Lepold L, Friedman J M. Positional cloning of the mouse obese gene and its human homologue. Nature 1994; 372:425-32.
2. Cosidine R V, Sinha M K, Heiman M L, et al. Serum immunoreactive-leptin concentrations in normal-weight and obese humans. N Engl J Med 1996; 334:292-5.
3. Ahima R S, Prabakaran D, Mantzoros C, et al. Role of leptin in the neuroendocrine response to fasting. Nature 1996: 382:250-2.
4. Montague C T, Farooqi I S, Whitehead J P, et al. Congenital leptin deficiency is associated with severe early onset obesity in humans. Nature 1997; 387:903-8.
5. Farooqi I S, Jebb S A, Langmack G. et al. Effects of recombinant leptin therapy in a child with congenital leptin deficiency. N Engl J Med 1999; 341:879-84.
6. Reitman M L, Arioglu E, Gavrilova O, Taylor S I. Lipoatrophy revisited. Trends Endoctrinol Metab. 2000; 11:410-6.
7. Lawrence R D. Lipodystrophy and hepatomegaly with diabetes, lipaemia, and other metabolic disturbances: a case throwing new light on the action of insulin. Lancet 1946; 1:724-731 and 773-775.
8. Magre J. Delepine M. Khallouf E, et al. Identification of the gene altered in Berardinelli-Seip congenital lipodystrophy on chromosome 11q13. Nat Genet 2001; 28:365-70.
9. Gavrilova O, Marcus-Samuela B; Graham D, et al. Surgical implantation of adipose tissue reverses diabetes in lipoatrophic mice. J Clin Invest 2000; 105: 271-8.
10. Shimomura I, Hammer R E, Ikemoto S, Brown M S, Goldstein J L. c Leptin reverses insulin resistance and diabetes mellitus in mice with congenital lipodystrophy. Nature 1999; 401:73-6.
11. Peters A L, Schriger D L. The new diagnostic criteria for diabetes: the impact on management of diabetes and macrovascular risk factors. Am J Med 1998; 105:15s-19s.
12. Garg A, Fleckenstein I L, Peshock R M, Grundy S M. Peculiar distribution of adipose tissue in patients with congenital generalized lipodystrophy. J Clin Endocrinol Metab 1992; 75:358-61.
13. Garg A Peshock R M, Fleckenstein J L. Adipose tissue distribution pattern in patients with familiar partial lipodystrophy (Dunnigan variety). I Clin Endocrinol Metab 1999; 84:170-4.
14. Cao H, Hegele R A. Nuclear Lamin A/C R482Q mutation in Canadian kindreds with Dunnigan-type familial partial lipodystrophy. Hum Mol Genent 2000; 9:109-12.
15. Harrision L C, Martin F I, Melick R4. Correlation between insulin receptor binding in isolated fat cells and insulin sensitivity in obese human subjects. J Clin Invest 1976; 58:1435-41.
16. Lambrinoudaki I, Georgiou E, Douskas G, Tsckes G, Kyriakidis M, Proukakis C. Body composition assessment by dual-energy x-ray absorptionmetry: comparison of prone and supine measurements. Metabolism 1998; 47:1379-82.
17. Abate N. Bums D, Peshock R M, Garg A, Grundy S M. Estimation of adipose tissue mass by magnetic resonance imaging: validation against dissection in human cadavers. J Lipid Res 1994; 35:1490-6.
18. Feskanich D, Rimm E B, Giovannucci E I, et al., Reproducibility and validity of food intake measurements from a semiquantitative food frequency questionnaire. J Am Diet Assoc 1993; 93:790-6.
19. Hahn G, Meeker W. Statistical Intervals: a guide to practitioners. New York: John Wiley and Sons, 1991.
20. Manton N D, Lipsett J, Moore D J, Davidson G P, Bourne A J, Couper R T. Non-alcoholic steatohepatitis in children and adolescents, Med J Aust 2000; 173:476-9.
21. Berasain C. Betes M. Panizo A, et al. Pathological and virological findings in patients with persistent hypertransaminasaemia of unknown etiology. Gut 2000:47:429-35.
22. Luyckx F H, Lefebvre P J, Scheen A J. Non-alcoholic steatohepatitis: association with obesity and insulin resistance, and influence of weight loss. Diabetes Metab 2000; 26:98-106.
23. Bolan C, Arioglu E, Gorden E, Taylor S, Lietman S. Intensive, long-term plasma exchange therapy for severe hypertriglyceridemia in acquired generalized lipoatrophy. J Clin Endocrin and Metab (submitted).
24. Intensive blood-glucose control with sulphonylureas or insulin compared with conventional treatment and risk of complications in patients with type 2 diabetes (UKPDS 33). UK Prospective Diabetes Study (UKPDS) Group. Lancet 1998; 352:837-53.
25. Kreisberg R A. Diabetic dyslipidemia. Am J Cardiol 1998; 82:67 U-73U
26. Gotto A M, Jr. Triglyceride as a risk factor for coronary artery disease. Am J Cariol 1998; 82: 22Q25Q.
27. Garg A., Lipodystrophies, Am J Med 2000; 108:143-52.
28 Arioglu E, Duncan-Morin J, Sebring N, et al. Efficacy and safety of troglitazone in the treatment of lipodystrophy syndromes. An Intern Med 2000; 133:263-74.

29. Trygstad O, Seip M. Oseid S. Lipodystrophic diabetes treated with fenfluramine. Int J Obes 1977: 1:287-92.
30. Ebihara K, Ogawa Y, Masuzaki H, et al. Transgenic overexpression of leptin rescues insulin resistance and diabetes in a mouse model of lipoatrophic diabetes. Diabetes 2001; 50:1440-8.
31. Campfield L A, Smith F J, Guisez Y, Devos R, Burn P. Recombinant mouse OB protein: evidence for a peripheral signal linking adiposity and central neural networks. Science 1995: 269:546-9.
32. Halaas J L. Gajiwala K S, Maffei M, et al. Weight-reducing effects of the plasma protein encoded by the obese gene. Science 1995; 269:543-6.
33. Pelleymounter M A, Cullen J M, Baker M B, et al. Effects of the obese gene product on body weight regulation in ob/ob mice. Science 1995; 269:540-3.
34. Mantzoros C S, Flier j S. Editorial: leptin as a therapeutic agent-trials and tribulations. J Clin Endocrinol Metab 2000; 85:4000-2.
35. Heymsfield S B, Greenberg A S, Fujioka K, et al. Recombinant leptin for weight loss in obese and lean adults: a randomized, controlled, dose-escalation trial [see comments]. Jama 1999; 282:1568-75.
36. Burant C F, Sreenan S. Hirano K, et al. Troglitazone action is independent of adipose tissue. J Clin Invest 1997; 100: 2900-8.
37. Moitra J, Mason M M, Olive M, et al. Life without white fat: a transgenic mouse. Genes Dev 1998; 12: 3168-81.
38. Shimomura I, Hammer R E, Richardson J A, et al. Insulin resistance and diabetes mellitus in transgenic mice expressing nuclear SREBP-1c in adipose tissue: model for congenital generalized lipodystrophy. Genes Dev 1998; 12:3182-94.
39. Shimomura I, Matsuda M. Hammer R E, Bashmakov Y, Brown M S, Goldstein J L. Decreased IRS-2 and increased SREBP-1c lead to mixed insulin resistance and sensitivity in livers of lipodystrophic and ob/ob mice, Mol Cel 2000; 6:77-86.
40. Unger R H. Lipotoxicity in the pathogenesis of obesity-dependent NIDDM, Genetic and clinical implications. Diabetes 1995; 44:863-70.
41. Unger R H, Zhou Y T, Orci L. Regulation of fatty acid homeostasis in cells: novel role of leptin. Proc Natl Acad Sci USA 1999; 96:2327-32.
42. Yamauchi T, Kamon J, Waki H, et al. The fat-derived hormone adiponectin reverses insulin resistance associated with both lipoatrophy and obesity. Nat Med 2001; 7:941-6.
43. Fruebis J. Tsao T S, Javorschi S, et al. Proteolytic cleavage product of 30-kDa adipocyte complement-related protein increases fatty acid oxidation in muscle and causes weight loss in mice. Proc Natl Acad Sci USA 2001; 98:2005-10.
44. Berg A H, Cumbs T P, Du X, Brownlee M, Scherer P E. The adipocyte-secreted protein Acrp30 enhances hepatic insulin action. Nat Med 2001; 7:947-53.

---

We claim:

1. A method of treating diabetes associated with an inherited or an acquired form of lipoatrophy in a human in need thereof comprising administering to the human a therapeutically effective amount of recombinant methionyl human leptin to treat the diabetes.

2. The method of claim 1, wherein the human has a leptin level of 4 ng/mi or less before administration of recombinant methionyl human leptin.

3. The method of claim 1, wherein the human has a leptin level of 2 ng/ml or less before administration of recombinant methionyl human leptin.

4. The method of claim 1, wherein the lipoatrophy is an acquired form of lipoatrophy.

5. The method of claim 1, wherein the lipoatrophy is an inherited, form of lipoatrophy.

6. The method of claim 5, wherein the inherited form of lipoatrophy is congenital generalized, lipoatrophy or familial partial lipodystrophy (FPLD).

7. The method of claim 1, wherein the recombinant methionyl human leptin is administered subcutaneously.

8. The method of claim 1, wherein the recombinant methionyl human leptin is administered together with at least one of a pharmaceutically acceptable carrier and a pharmaceutically acceptable diluent.

9. The method of claim 1, wherein the method further comprises administering at least one compound selected from the group consisting of a thiazolidinedione, a fibrate, a statin and metformin.

10. A method of treating hypertriglyceridemia associated with an inherited or an acquired form of lipoatrophy in a human in need thereof comprising administering to the human a therapeutically effective amount of recombinant methionyl human leptin to treat the hypertriglyceridemia.

11. The method of claim 10, wherein the human has a leptin level of 4 ng/ml or less before administration of recombinant methionyl human leptin.

12. The method of claim 10, wherein the human has a leptin level of 2 ng/ml or less before administration of recombinant methionyl human leptin.

13. The method of claim 10, wherein the lipoatrophy is an acquired form of lipoatrophy.

14. The method of claim 10, wherein the lipoatrophy is an inherited form of lipoatrophy.

15. The method of claim 10, Wherein the recombinant methionyl human leptin is administered subcutaneously.

16. The method of claim 10, wherein the recombinant methionyl human leptin is administered together with at least one of a pharmaceutically acceptable carrier and a pharmaceutically acceptable diluent.

17. The method of claim 10, wherein the method further comprises administering at least one compound selected from the group consisting of a thiazolidinedione, fibrate, a statin and metformin.

18. A method of treating a metabolic abnormality associated with an inherited or an acquired fowl of lipoatrophy in a human in need thereof comprising administering to the human a therapeutically effective amount of recombinant methionyl human leptin to treat the metabolic abnormality.

19. The method of claim 18, wherein the human has a leptin, level of 4 ng/ml or less before administration of recombinant methionyl human leptin.

20. The method of claim 18, wherein the human has a leptin level of 2 ng/ml or less before administration of recombinant meihionyl human leptin.

21. The method of claim 18, wherein the lipoatrophy is an acquired form of lipoatrophy.

22. The method of claim 18, wherein the lipoatrophy is an inherited form of lipoatrophy.

23. The method of claim 18, wherein the metabolic abnormality is diabetes, hypertriglyceridemia, hyperglycemia, dyslipidemia, hyperlipidemia, hypercholesterolemia, atherosclerosis, restenosis, fatty liver, steatohepatitis, hepatomegaly, or insulin resistance.

24. The method of claim 18, wherein the metabolic abnormality is dyslipidemia.

25. The method of claim 18, wherein the metabolic abnormality is hyperlipidemia.

26. The method of claim 18, wherein the metabolic abnormality is hypercholesterolemia.

27. The method of claim 18, wherein the metabolic abnormality is atherosclerosis.

28. The method of claim 18, wherein the metabolic abnormality is vascular restenosis.

29. The method of claim 18, wherein the metabolic abnormality is fatty liver.

30. The method of claim 18, wherein the metabolic abnormality is steatohepatitis.

31. The method of claim 18, wherein the metabolic abnormality is hepatomegaly.

32. The method of claim 18, wherein the metabolic abnormality is insulin resistance.

33. The method of claim 18, wherein the recombinant methionyl human leptin is administered subcutaneously.

34. The method of claim 18, wherein the recombinant methionyl human leptin is administered together with at least one of a pharmaceutically acceptable carrier and a pharmaceutically acceptable diluent.

35. The method of claim 18, wherein the method further comprises administering at least one compound selected from the group consisting of a thiazolidinedione, a fibrate, a statin and metformin.

* * * * *

SEQUENCE LISTING

```
<160> NUMBER OF SEQ ID NOS: 2

<210> SEQ ID NO 1
<211> LENGTH: 146
<212> TYPE: PRT
<213> ORGANISM: Artificial
<220> FEATURE:
<223> OTHER INFORMATION: Artificial sequence: Recombinant Leptin Human
      146 (rHu-Leptin 1-146)

<400> SEQUENCE: 1

Val Pro Ile Gln Lys Val Gln Asp Asp Thr Lys Thr Leu Ile Lys Thr
 1               5                  10                  15

Ile Val Thr Arg Ile Asn Asp Ile Ser His Thr Gln Ser Val Ser Ser
                20                  25                  30

Lys Gln Lys Val Thr Gly Leu Asp Phe Ile Pro Gly Leu His Pro Ile
            35                  40                  45

Leu Thr Leu Ser Lys Met Asp Gln Thr Leu Ala Val Tyr Gln Gln Ile
        50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145
```

```
<210> SEQ ID NO 2
<211> LENGTH: 145
<212> TYPE: PRT
<213> ORGANISM: Artificial
<220> FEATURE:
<223> OTHER INFORMATION: Artificial sequence: Recombinant leptin Human
      145 (rHu-Leptin 1-145)

<400> SEQUENCE: 2

Val Pro Ile Gln Lys Val Gln Asp Asp Thr Lys Thr Leu Ile Lys Thr
1               5                   10                  15

Ile Val Thr Arg Ile Asn Asp Ile Ser His Thr Ser Val Ser Ser Lys
            20                  25                  30

Gln Lys Val Thr Gly Leu Asp Phe Ile Pro Gly Leu His Pro Ile Leu
        35                  40                  45

Thr Leu Ser Lys Met Asp Gln Thr Leu Ala Val Tyr Gln Gln Ile Leu
    50                  55                  60

Thr Ser Met Pro Ser Arg Asn Val Ile Gln Ile Ser Asn Asp Leu Glu
65                  70                  75                  80

Asn Leu Arg Asp Leu Leu His Val Leu Ala Phe Ser Lys Ser Cys His
            85                  90                  95

Leu Pro Trp Ala Ser Gly Leu Glu Thr Leu Asp Ser Leu Gly Gly Val
            100                 105                 110

Leu Glu Ala Ser Gly Tyr Ser Thr Glu Val Val Ala Leu Ser Arg Leu
        115                 120                 125

Gln Gly Ser Leu Gln Asp Met Leu Trp Gln Leu Asp Leu Ser Pro Gly
    130                 135                 140

Cys
145
```